United States Patent
Fujii et al.

(10) Patent No.: US 12,103,543 B2
(45) Date of Patent: Oct. 1, 2024

(54) COMFORT DRIVING DATA COLLECTION SYSTEM, DRIVING CONTROL DEVICE, METHOD, AND PROGRAM

(71) Applicant: NEC Corporation, Tokyo (JP)

(72) Inventors: Asako Fujii, Tokyo (JP); Yusuke Koitabashi, Tokyo (JP); Takuroh Kashima, Tokyo (JP); Yuki Chiba, Tokyo (JP); Kenji Sobata, Tokyo (JP)

(73) Assignee: NEC CORPORATION, Tokyo (JP)

( * ) Notice: Subject to any disclaimer, the term of this patent is extended or adjusted under 35 U.S.C. 154(b) by 267 days.

(21) Appl. No.: 17/627,969

(22) PCT Filed: May 22, 2020

(86) PCT No.: PCT/JP2020/020333
§ 371 (c)(1),
(2) Date: Jan. 18, 2022

(87) PCT Pub. No.: WO2021/014738
PCT Pub. Date: Jan. 28, 2021

(65) Prior Publication Data
US 2022/0274608 A1    Sep. 1, 2022

(30) Foreign Application Priority Data

Jul. 19, 2019 (JP) ................ 2019-133484

(51) Int. Cl.
*B60W 50/00* (2006.01)
*B60W 40/08* (2012.01)
*G06N 20/00* (2019.01)

(52) U.S. Cl.
CPC ........ *B60W 50/0098* (2013.01); *B60W 40/08* (2013.01); *G06N 20/00* (2019.01); *B60W 2540/221* (2020.02)

(58) Field of Classification Search
CPC ............ B60W 50/0098; B60W 40/08; B60W 2540/221; G06N 20/00
See application file for complete search history.

(56) References Cited

U.S. PATENT DOCUMENTS

2018/0268695 A1* 9/2018 Agnew ................. B60W 50/14
2019/0019087 A1* 1/2019 Fukui .................... G06V 20/593
(Continued)

FOREIGN PATENT DOCUMENTS

| JP | 2006-130121 A | 5/2006 |
| JP | 2010-519124 A | 6/2010 |

(Continued)

OTHER PUBLICATIONS

JP Office Communication for JP Application No. 2021-534561, mailed on Jan. 31, 2023 with English Translation.
(Continued)

*Primary Examiner* — Peter D Nolan
*Assistant Examiner* — Wae L Louie

(57) ABSTRACT

A comfort determination model learning unit 81 learns a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators. An individual data generation unit 82 generates individual data including explanatory variables, which are used in the comfort determination model, generated based on the comfort indicators of the subject during riding on a
(Continued)

vehicle, and driving situations of the vehicle when the comfort indicators are obtained. A driving data generation unit 83 generates comfortable driving data and uncomfortable driving data according to a comfort value calculated by applying the individual data to the comfort determination model.

9 Claims, 6 Drawing Sheets

(56) References Cited

U.S. PATENT DOCUMENTS

| 2020/0060597 | A1* | 2/2020  | Ogawa   | G06V 40/20 |
|---|---|---|---|---|
| 2020/0406906 | A1* | 12/2020 | Omari   | G05D 1/0223 |
| 2021/0122381 | A1* | 4/2021  | Ahn     | B60W 40/08 |
| 2021/0153796 | A1* | 5/2021  | De Weser| A61B 5/0205 |
| 2022/0067412 | A1* | 3/2022  | Takamoto| B60W 50/14 |
| 2022/0274608 | A1* | 9/2022  | Fujii   | A61B 5/18 |
| 2022/0330848 | A1* | 10/2022 | Ferraris| H04R 1/1083 |
| 2022/0388543 | A1* | 12/2022 | David   | B60W 60/0051 |
| 2023/0256994 | A1* | 8/2023  | Stumpf  | B60W 60/00 701/26 |
| 2023/0315783 | A1* | 10/2023 | Fujii   | G06F 16/583 382/305 |
| 2023/0373506 | A1* | 11/2023 | Adiprasito | G06V 20/597 |

FOREIGN PATENT DOCUMENTS

| JP | 2018-152072 A | 9/2018 |
|---|---|---|
| JP | 2018-160136 A | 10/2018 |
| WO | 2017/163538 A1 | 9/2017 |
| WO | 2018/109863 A1 | 6/2018 |

OTHER PUBLICATIONS

International Search Report for PCT Application No. PCT/JP2020/020333, mailed on Aug. 11, 2020.

English translation of Written opinion for PCT Application No. PCT/JP2020/020333, mailed on Aug. 11, 2020.

* cited by examiner

COMFORT DRIVING DATA COLLECTION SYSTEM, DRIVING CONTROL DEVICE, METHOD, AND PROGRAM

This application is a National Stage Entry of PCT/JP2020/020333 filed on May 22, 2020, which claims priority from Japanese Patent Application 2019-133484 filed on Jul. 19, 2019, the contents of all of which are incorporated herein by reference, in their entirety.

TECHNICAL FIELD

The present invention relates to a comfort driving data collection system, a driving control device, a comfort driving data collection method, a driving control method, a comfort driving data collection program, and a driving control program for collecting data indicating driving comfort.

BACKGROUND ART

In recent years, with the development of driving control technology, more comfortable driving control is desired. For example, individual drivers desire automated vehicles that they feel more comfortable in, and passengers who are not driving also desire to ride in vehicles that are more comfortable to drive.

For example, patent literature 1 describes a driving support device that contributes to improving or maintaining a riding condition. The driving support device described in patent literature 1 monitors a driving status of a vehicle and notifies a server installed outside the vehicle of the monitoring results. The server outputs a message for a suggestion (or vehicle control) using a knowledge database based on the notified contents.

CITATION LIST

Patent Literature

PTL 1: Japanese Patent Laid-Open No. 2018-160136

SUMMARY OF INVENTION

Technical Problem

On the other hand, it is difficult to define good or bad driving because the comfort felt by an individual differs from person to person, and it is also difficult to give specific instructions to others on how to drive in a good way as imagined by the individual. Therefore, for example, even in automatic driving, it is difficult to reflect individual preferences in driving.

Since the recommended information stored by the knowledge database described in patent literature 1 is in a general method, individual passengers do not necessarily feel comfortable with it. Therefore, even if the driving support device described in patent literature 1 is used, it is not necessarily possible to improve the comfort of individual passengers.

It is desirable to be able to collect a large number of data indicating individual comfort for each condition in order to be able to determine whether a condition during a ride is comfortable or not for each individual passenger. However, it is difficult to generate data indicating the comfort of each passenger for each situation during a ride by determining successively whether the passenger is comfortable or not. It is also difficult to use a device that is physically restraining to the driver.

Therefore, it is an exemplary object of the present invention to provide a comfort driving data collection system, a comfort driving data collection method, and a comfort driving data collection program, as well as a driving control device, a driving control method, and a driving control program, which can efficiently collect data indicating the comfort of a passenger according to a driving situation during a ride.

Solution to Problem

A comfort driving data collection system according to the exemplary aspect of the present invention includes a comfort determination model learning unit which learns a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, an individual data generation unit which generates, for each subject, individual data including explanatory variables, which are used in the comfort determination model, generated based on the comfort indicators of the subject during riding on a vehicle, and driving situations of the vehicle when the comfort indicators are obtained, and a driving data generation unit which calculates the comfort value by applying the individual data to the comfort determination model, and generates driving data indicating a comfortable driving situation and driving data indicating an uncomfortable driving situation according to the calculated comfort value.

A driving control device according to the exemplary aspect of the present invention includes a comfortable driving determination unit which determines that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and a comfortable driving information output unit which outputs information to control driving of the vehicle based on a determination result by the comfortable driving determination unit.

A comfort driving data collection method according to the exemplary aspect of the present invention includes learning a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, generating, for each subject, individual data including explanatory variables, which are used in the comfort determination model, generated based on the comfort indicators of the subject during riding on a vehicle, and driving situations of the vehicle when the comfort indicators are obtained, and calculating the comfort value by applying the individual data to the comfort determination model, and generating driving data indicating a comfortable driving situation and driving data indicating an uncomfortable driving situation according to the calculated comfort value.

A driving control method according to the exemplary aspect of the present invention includes determining that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and outputting information to control driving of the vehicle based on a determination result.

A comfort driving data collection program according to the exemplary aspect of the present invention causes a computer to execute a comfort determination model learning process of learning a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, an individual data generation process of generating, for each subject, individual data including explanatory variables, which are used in the comfort determination model, generated based on the comfort indicators of the subject during riding on a vehicle, and driving situations of the vehicle when the comfort indicators are obtained, and a driving data generation process of calculating the comfort value by applying the individual data to the comfort determination model, and generating driving data indicating a comfortable driving situation and driving data indicating an uncomfortable driving situation according to the calculated comfort value.

A driving control program according to the exemplary aspect of the present invention causes a computer to execute a comfortable driving determination process of determining that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and a comfortable driving information output process of outputting information to control driving of the vehicle based on a determination result.

Advantageous Effects of Invention

According to the exemplary aspect of the present invention, it is possible to efficiently collect data indicating the comfort of a passenger according to a situation during a ride.

DESCRIPTION OF EMBODIMENTS

Hereinafter, example embodiment of the exemplary aspect of the present invention is described with reference to the drawings.

Figure 1:
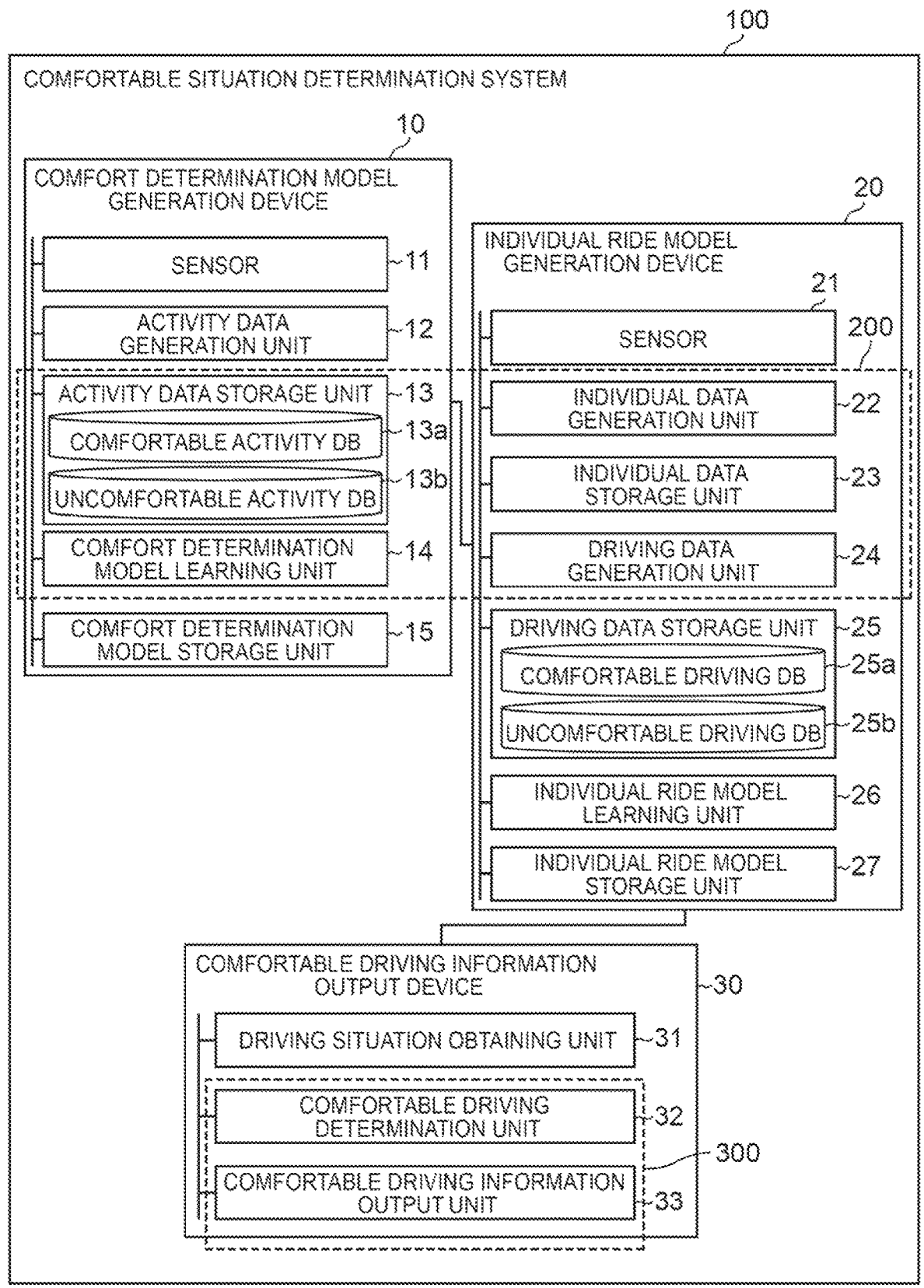
FIG. 1 It depicts a block diagram showing a configuration example of an example embodiment of a comfortable situation determination system.

FIG. 1 is a block diagram showing a configuration example of an example embodiment of a comfort driving data collection system and a comfortable situation determination system including a driving control device according to the exemplary aspect of the present invention. The comfortable situation determination system 100 of this example embodiment comprises a comfort determination model generation device 10, an individual ride model generation device 20, and a comfortable driving information output device 30.

A comfort determination model generation device 10 is a device for generating a comfort determination model for determining a degree of comfort during a ride felt by each individual. The individuals assumed in this example embodiment include not only a driver who actually drives a vehicle but also passengers of the vehicle. In the following description, the target individual may be referred to simply as a target.

The comfort determination model generation device 10 of this example embodiment includes a sensor 11, an activity data generation unit 12, an activity data storage unit 13, a comfort determination model learning unit 14, and a comfort determination model storage unit 15.

The sensor 11 is a sensor that detects an indicator by which whether or not a subject can be comfortable measured. In the following description, an indicator by which whether or not a subject can be comfortable measured is referred to as a comfort indicator. The comfort indicator is not limited to an indicator by which whether or not a subject can be comfortable measured directly, but can also be information by which whether or not a subject can be comfortable measured indirectly. The comfort indicator is, for example, a human life characteristic (pulse, blood pressure, body temperature, etc.) or a body maintenance state (change in center of gravity, etc.). Specifically, the sensor 11 is a heart rate meter to obtain a heartbeat, an electroencephalograph to obtain an electroencephalogram, a thermo camera to obtain a body temperature and a room temperature, a thermometer to obtain a body temperature, a sound collecting microphone to obtain a voice color and a noise, and an AI (Artificial Intelligence) speaker to obtain a voice color. In addition to the above, a weight sensor to obtain body sway or center of gravity, an infrared sensor to obtain heartbeat, pulse, blood pressure, stress level, and oxygen saturation, and an odor sensor to obtain odor may be used as the sensor 11. In addition, a smartphone or a camera capable of obtaining various information such as facial expression, body sway, number of blinks, facial color, number of specific movements, voice color, sleepiness, and concentration may be used as the sensor 11. There may be a plurality of comfort sensors 11, and it is preferable that the sensor is capable of obtaining a comfort indicator without restraining the subject.

In this example embodiment, the situation in which the sensor 11 detects the comfort indicator of the subject is not limited to the time of riding. However, in this example embodiment, it is assumed that the situation of the activity in which the sensor 11 detects the comfort indicator of the subject is identifiable, and it is assumed that it is predetermined whether the activity is a comfortable activity or an uncomfortable activity for the subject.

For example, in terms of vision, a situation where the subject watches a favorite TV program (for example, a drama) can be said to be a comfortable activity situation, while a situation where the subject watches an uninteresting TV program (for example, stock price introduction) can be said to be an uncomfortable activity situation. In terms of hearing, a situation where the subject talks with a close friend or listens to a favorite music can be said to be a comfortable activity situation, while a situation where the subject talks with a new acquaintance or listens to an unpleasant sound (for example, scratching the blackboard) can be said to be an uncomfortable activity situation.

From the tactile point of view, a situation where the subject spends time in a cool place, has your shoulders rubbed, and takes deep breaths can be said to be comfortable activity situations, while a situation where the subject spends time in a hot and humid place, has the back of your hand pinched, and keeps eyes open for one minute can be said to be uncomfortable activity situations. From the point of view of taste, a situation where the subject eats a favorite food (for example, cake) is a comfortable activity situation, while the situation where the subject eats a disliked food (for example, green pepper) is an uncomfortable activity situation.

Furthermore, from the point of view of the sense of smell, a situation where the subject smells a favorite smell (for example, citrus) can be said to be comfortable activity situation, while a situation where the subject smells a disliked smell (for example, garbage) can be said to be an uncomfortable activity situation. Thus, in this example embodiment, the sensor 11 detects a comfort indicator according to a comfortable or uncomfortable situation in which the subject is engaged in an activity. However, the above described activities are examples, and it is sufficient if a situation of any activity that the subject feels comfortable or uncomfortable is assumed.

The activity data generation unit 12 generates activity data where a comfort indicator detected by the sensor 11 is associated with information indicating comfortable or not when the comfort indicator is detected. Specifically, the activity data generation unit 12 generates either or both of the comfortable activity data where the comfort indicator when an activity classified as a comfortable activity is performed is associated with a teacher label indicating comfort, and the uncomfortable activity data where the comfort indicator when an activity classified as an uncomfortable activity is performed is associated with a teacher label indicating discomfort.

For example, suppose that the heart rate is obtained by the sensor 11 in a situation where the subject is watching a favorite TV program. At this time, the obtained heart rate can be said to be a comfort indicator during a comfortable activity. In this case, the activity data generation unit 12 may generate comfortable activity data where the comfort indicator in this situation is associated with a teacher label indicating the comfort. Specifically, for example, suppose that the subject watches a favorite TV program for one hour, and the heart rate per 60 seconds at that time is collected sequentially by the sensor 11. In this case, the activity data generation unit 12 may sequentially collect the heart rate per 60 seconds and generate the comfort activity data where the collected heart rate is associated with a teacher label indicating comfort in a time series.

Similarly, suppose that the heart rate is obtained by the sensor 11 in a situation where the user is watching a TV program in which the user has no interest. At this time, the obtained heart rate can be said to be a comfort indicator during an uncomfortable activity. In this case, the activity data generation unit 12 may generate comfortable activity data where the comfort indicator at this time is associated with a teacher label indicating discomfort. Similar to the above, suppose, for example, that a TV program in which the subject is not interested is watched for one hour, and the heart rate per 60 seconds at that time is collected sequentially by the sensor 11. In this case, the activity data generation unit 12 may sequentially collect the heart rate per 60 seconds and generate the discomfort activity data where the collected heart rate is associated with a teacher label indicating discomfort in a time series.

Figure 2:
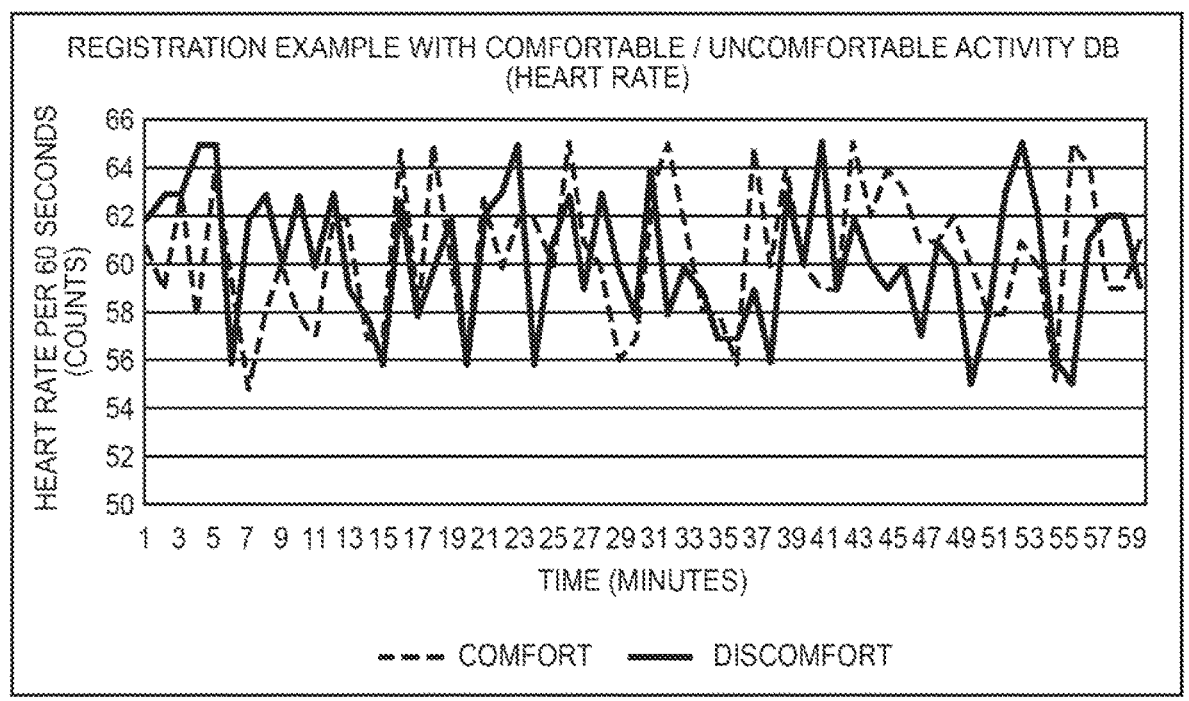
FIG. 2 It depicts an explanatory diagram showing an example of activity data.

FIG. 2 is an explanatory diagram showing an example of activity data. The example shown in FIG. 2 indicates that the activity data generation unit 12 aggregates the heart rate per 60 seconds by comfort or discomfort to generate comfortable activity data and uncomfortable activity data, which are displayed in a time series. The activity data generation unit 12 may also aggregate other data, such as the number of blinks per 60 seconds. The activity data generation unit 12 stores the generated activity data in the activity data storage unit 13.

The activity data storage unit 13 stores the generated activity data. Specifically, the activity data storage unit 13 may store the comfortable activity data and the uncomfortable activity data in the comfortable activity DB (Database) 13a and the uncomfortable activity DB 13b, respectively. The activity data storage unit 13 is realized, for example, by a magnetic disk or the like.

The comfort determination model learning unit 14 uses the comfort activity data and the discomfort activity data as training data to learn a comfort determination model in which a degree of comfort (hereinafter, sometimes referred to as a comfort value) as an objective variable and each of the comfort indicators obtained by the sensor 11 as an explanatory variable. The comfort activity data and the discomfort activity data may be referred to as the first training data in order to distinguish them from the training data described below.

The comfort determination model learning unit 14 may use a comfort indicator detected by the sensor 11 itself as an explanatory variable, or may use aggregated comfort indicator over a certain period of time as an explanatory variable. For example, the comfort determination model learning unit 14 may use, as described above, the heart rate per 60 seconds or the number of blinks per 60 seconds as an explanatory variable.

The method by which the comfort determination model learning unit 14 learns the comfort determination model is arbitrary. For example, the comfort determination model learning unit 14 may learn the comfort determination model using multiple regression analysis. In the above example, when the heart rate per 60 seconds and the number of blinks per 60 seconds are used as explanatory variables, the comfort determination model can be expressed as follows.

Comfort level=$a$×(heart rate per 60 seconds)+$b$×(number of blinks per 60 seconds)+$c$ The comfort determination model learning unit 14 stores the generated comfort determination model in the comfort determination model storage unit 15.

The comfort determination model storage unit 15 stores the comfort determination model for each subject. The comfort determination model storage unit 15 is connected to the individual ride model generation device 20, and is used when generating driving data as described below. The comfort determination model storage unit 15 is realized, for example, by a magnetic disk or the like.

The individual ride model generation device 20 includes a sensor 21, an individual data generation unit 22, an individual data storage unit 23, a driving data generation unit 24, a driving data storage unit 25, an individual ride model learning unit 26, and an individual ride model storage unit 27.

The sensor 21, like the sensor 11, is a sensor that detects a comfort indicator of the subject. Specifically, the sensor 21 is mounted, for example, on a vehicle for determining comfort, and detects a comfort indicator of the subject when riding the vehicle. The content of the comfort indicator detected by the sensor 21 is the same as the content of the comfort indicator detected by the sensor 11.

The individual data generation unit 22 generates individual data of a subject (hereinafter, simply referred to as "individual data") to be applied to a comfort determination model from a comfort indicator of the subject during a ride detected by the sensor 21. Specifically, for each subject, the individual data generation unit 22 generates individual data including explanatory variables, which are generated based on the detected comfort indicators, to be used in the comfort determination model, and driving situations of the vehicle when the comfort indicators are detected.

In the above described example, the individual data generation unit 22 may generate individual data where explanatory variables aggregating the heart rate per 60 seconds and the number of blinks per 60 seconds obtained by the sensor 21 are associated with the driving situation of the vehicle at that time. The driving situation is, for example, operation information of the vehicle, such as an accelerator opening degree, a brake pressure, and an angle of steering wheel operation. The individual data generation unit 22 stores the generated individual data in the individual data storage unit 23.

The individual data storage unit 23 stores individual data of the subject. The individual data storage unit 23 is realized, for example, by a magnetic disk or the like.

The driving data generation unit 24 applies the individual data to the comfort determination model of the subject to generate driving data in which the degree of comfort (i.e., the comfort value) of the subject is determined. Specifically, the driving data generation unit 24 obtains a comfort determination model of the subject from the comfort determination model storage unit 15, applies the individual data to the obtained comfort determination model, and calculates the comfort value. Then, the driving data generation unit 24 generates driving data indicating a comfortable driving situation (hereinafter, referred to as "comfortable driving data") and driving data indicating an uncomfortable driving situation (hereinafter, referred to as "uncomfortable driving data") according to the calculated comfort values.

The driving data generation unit 24 may generate the comfortable driving data and the uncomfortable driving data by comparing the predetermined threshold and the calculated comfort value. For example, when the comfort value exceeds the threshold, the driving data generation unit 24 may generate, as the comfortable driving data, driving data where the driving situation included in the individual data is associated with a comfortable driving flag. On the other hand, if the comfort value is below the threshold, the driving data generation unit 24 may generate, as the uncomfortable driving data, driving data where the driving situation included in the individual data is associated with an uncomfortable driving flag.

Hereinafter, the method that is generated driving data is explained using specific examples. For example, suppose that the individual data includes "heart rate per 60 seconds" and "number of blinks per 60 seconds" during a ride, as well as data indicating the characteristic of the individual during a ride (driving situation). The driving data generation unit 24 applies this individual data to the comfort determination model to calculate a comfort value. Here, suppose that the comfort value is output as 0.7. Suppose also that the threshold for determining as comfortable is set to 0.5. In this case, since the comfort value exceeds the threshold, the driving data generation unit 24 sets a comfortable driving flag to the individual data at that time, and generates data including the comfortable driving flag and the driving situation as driving data.

Figure 3:
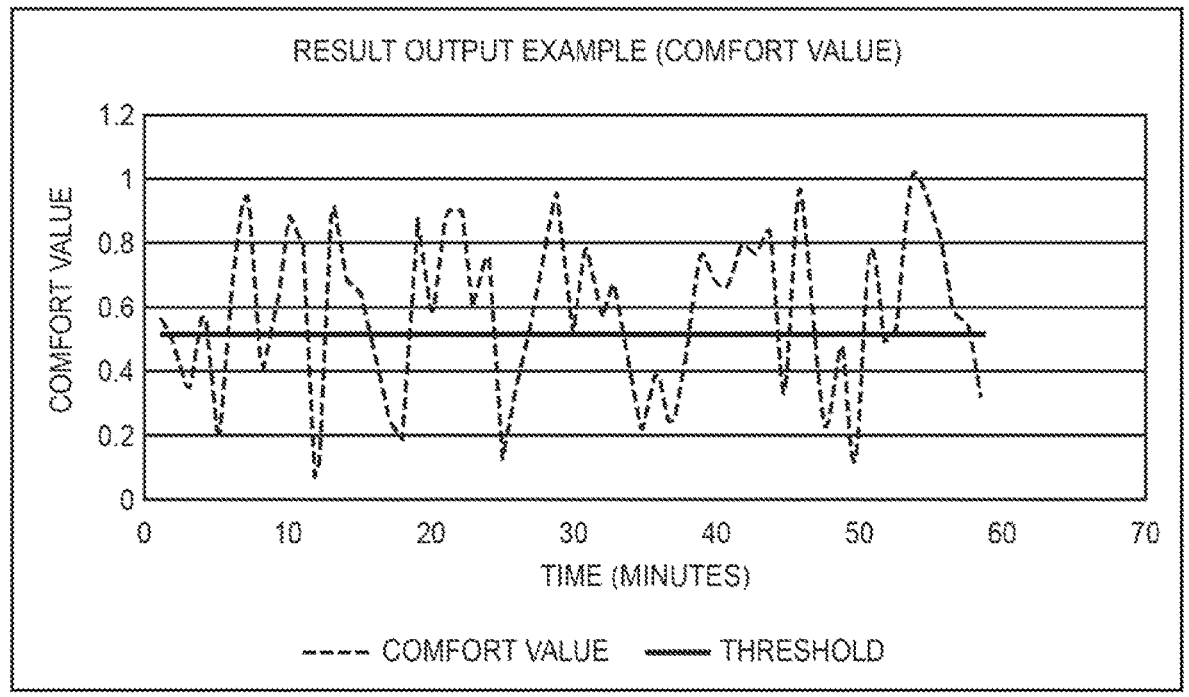
FIG. 3 It depicts an explanatory diagram showing an example of a process of generating driving data.

FIG. 3 is an explanatory diagram showing an example of a process of generating driving data. The graph illustrated in FIG. 3 represents the transition of the comfort value in a time series. In the example shown in FIG. 3, it is assumed that the threshold is set to 0.5. At this time, the driving data generation unit 24 may generate the driving data by setting the comfortable driving flag to the individual data whose comfort value at the time of determination exceeds the threshold (0.5) (or by setting the uncomfortable driving flag to the individual data whose comfort value is below the threshold).

The driving data generation unit 24 stores the generated driving data in the driving data storage unit 25. The driving data is data in which a comfortable driving flag (uncomfortable driving flag) is set according to the driving situation (access acceleration, brake pressure, and angle of steering wheel operation), as described above.

The driving data storage unit 25 stores the driving data. Specifically, the driving data storage unit 25 may store the comfortable driving data and the uncomfortable driving data in the comfortable driving DB 25a and the uncomfortable driving DB 25b, respectively. The driving data storage unit 25 is realized, for example, by a magnetic disk or the like.

The individual ride model learning unit 26 uses the generated driving data as training data to learn an individual ride model that indicates a comfort situation of an individual according to the driving situation. The driving data used by the individual ride model learning unit 26 for learning may be described as the second training data, in order to distinguish it from the training data used by the comfort determination model learning unit 14.

The method by which the individual ride model learning unit 26 learns the individual ride model is arbitrary. For example, the individual ride model learning unit 26 may learn an individual ride model (reward function) using inverse reinforcement learning. The individual ride model learning unit 26 stores the learned individual ride model in the individual ride model storage unit 27.

The individual ride model storage unit 27 stores the generated individual ride model in the individual ride model storage unit 27. The individual ride model storage unit 27 is connected to a comfortable driving information output device 30 and is used to determine a comfortable situation. The individual ride model storage unit 27 is realized, for example, by a magnetic disk or the like.

A comfortable driving information output device 30 includes a driving situation obtaining unit 31, a comfortable driving determination unit 32, and a comfortable driving information output unit 33.

The driving situation obtaining unit 31 obtains the driving situation of the vehicle in which the subject is riding. The driving situation obtaining unit 31 is realized, for example, by an in-vehicle sensor or the like, and obtains accelerator opening, brake pressure, angle of steering wheel operation and the like as described below.

The comfortable driving determination unit 32 determines the driving that is comfortable for the subject based on the individual ride model. For example, when the individual ride model (reward function) is generated by inverse reinforcement learning, the comfortable driving determination unit 32 may estimate the driving that optimizes the reward as comfortable driving. Specifically, the comfortable driving determination unit 32 may generate a specific driving operation (optimal behavior) that approaches comfortable driving (reward) based on the information stored as comfortable driving data.

The comfortable driving information output unit 33 outputs the determination result by the comfortable driving determination unit 32. The comfortable driving information output unit 33 may output result of comparing the driving situation of the vehicle in which the subject is riding and the determination result by the individual ride model. The comfortable driving information output unit 33 may output the determination result sequentially, or may output the determination result when the predetermined criteria for notification are satisfied.

For example, in the case where the driving that is determined to be comfortable is continuous for five minutes (the driving situation in which the comfortable driving flag is set is continuous for five minutes), the comfortable driving information output unit 33 may output a determination result of the content "It is good operation". On the other hand, for example, when the driving that is determined to be uncomfortable is continuous for five minutes (the driving situation in which the uncomfortable driving flag is set is continuous for five minutes), the comfortable driving information output unit 33 may output a determination result of the content of a specific operation (for example, a content of "step on the accelerator gently").

The comfortable driving information output unit 33 may output the determination result to various output devices (audio output or output to an instrument panel) as described below. In addition, the comfortable driving information output unit 33 may output information for controlling the driving of the vehicle to a control unit (not shown) of the vehicle based on the determination result by the comfortable driving determination unit 32. Specifically, the comfortable driving information output unit 33 may notify a control method to the control unit of the vehicle so that the comfort can be maintained in the case of automatic driving.

In this example embodiment, the comfort determination model learning unit 14 included in the comfort determination model generation device 10, and the individual data generation unit 22 and the driving data generation unit 24 included in the individual ride model generation device 20 can generate driving data using the activity data and the individual data. Therefore, a system that includes at least these components can be referred to as the comfort driving data collection system 200.

In addition, the comfortable driving determination unit 32 and the comfortable driving information output unit 33 can control the driving of the vehicle so that it feels comfortable for the subject using the individual ride model learned from the driving data generated by applying the individual data to the comfort determination model. Therefore, the device including the comfortable driving determination unit 32 and the comfortable driving information output unit 33 can be referred to as the driving control device 300.

The driving control device 300 (more specifically, the comfortable driving information output unit 33) may, for example, make the output device of the vehicle output information indicating comfortable driving. Specific examples of the output include making the instrument panel display "Please step on the accelerator gently" and making the speaker output "Please step on the accelerator gently".

In addition, the driving control device 300 (the comfortable driving information output unit 33) may also notify the control unit of the automatic vehicle of various signals to realize comfortable driving. For example, when it is desired to control the accelerator operation gently, the driving control device 300 may output an operation signal to the control unit of the automatic vehicle to apply the accelerator gently.

The activity data generation unit 12, the comfort determination model learning unit 14, the individual data generation unit 22, the driving data generation unit 24, and the individual ride model learning unit 26 are realized by a processor of a computer (for example, a CPU (Central Processing Unit), GPU (Graphics Processing Unit)) operating according to the program (comfort driving data collection program).

For example, the program may be stored in a memory unit (not shown) of the comfort determination model generation device 10 or the individual ride model generation device 20, and the processor may read the program and, according to the program, operate as the activity data generation unit 12, the comfort determination model learning unit 14, the individual data generation unit 22, the driving data generation unit 24, and the individual ride model learning unit 26. The functions of the comfortable situation determination system may be provided in a SaaS (Software as a Service) format.

The activity data generation unit 12, the comfort determination model learning unit 14, the individual data generation unit 22, the driving data generation unit 24, and the individual ride model learning unit 26 may each be realized by dedicated hardware. Some or all of each of the components in each of the devices may be realized by a general-purpose or dedicated circuitry, processor, or the like, or a combination thereof. These may comprise a single chip or a plurality of chips connected through a bus. Some or all of each component in each device may be realized by a combination of the above described circuits, etc. and a program.

When some or all of the components in the comfortable situation determination system are realized by a plurality of information processing devices, circuits, or the like, the plurality of information processing devices, circuits, or the like may be centrally arranged or distributed. For example, the information processing devices, circuits, and the like may be implemented as a client-server system, a cloud computing system, and the like, each of which is connected through a communication network.

The comfort determination model generation device 10, the individual ride model generation device 20, and the comfortable driving information output device 30 may each be realized by the same device, or each configuration of each device may be combined with a configuration of another device to be realized as a separate device.

Figure 4:
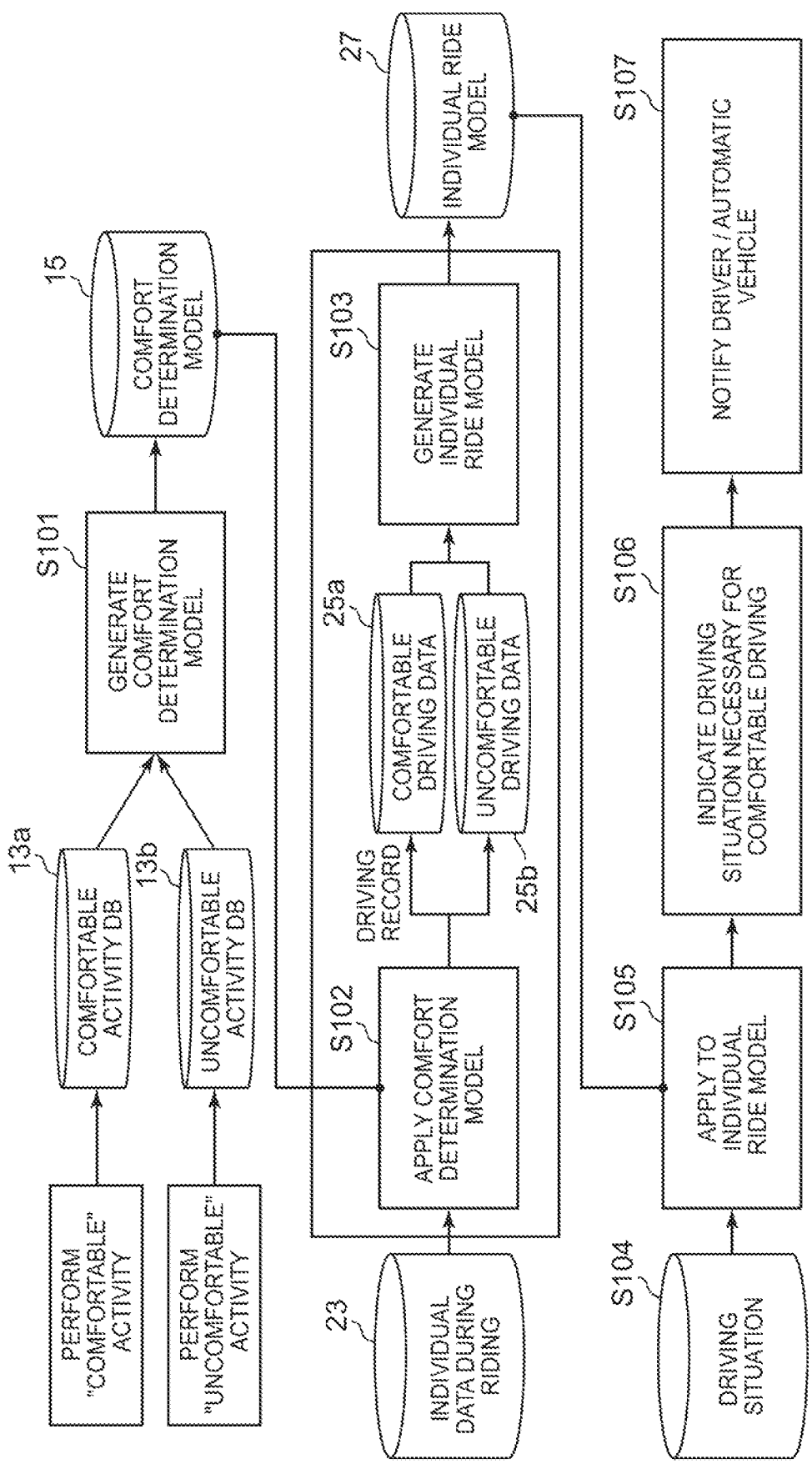
FIG. 4 It depicts an explanatory diagram showing an operation example of a comfortable situation determination system.

Next, an operation example of the comfortable situation determination system 100 of this example embodiment will be described. FIG. 4 is explanatory diagram showing an operation example of the comfortable situation determination system 100 of this example embodiment. The activity data generation unit 12 generates the comfortable activity data from the comfort indicators in the situation of the "comfortable" activity detected by the sensor 11, and stores it in the comfortable activity DB 13*a* of the activity data storage unit 13. Similarly, the activity data generation unit 12 generates uncomfortable activity data from the comfort indicators in a situation of "uncomfortable" activity detected by the sensor 11, and stores it in the uncomfortable activity DB 13*b* of the activity data storage unit 13.

The comfort determination model learning unit 14 learns the comfort determination model from the comfortable activity data and the uncomfortable activity data (step S101). The comfort determination model learning unit 14 stores the generated comfort determination model in the comfort determination model storage unit 15.

Thereafter, the individual data generation unit 22 generates individual data from the comfort indicators of a passenger riding in the vehicle, which are detected by the sensor 21, and stores the individual data in the individual data storage unit 23. The driving data generation unit 24 applies the individual data to the comfort determination model to generate comfortable driving data and uncomfortable driving data (step S102), and stores them in the comfortable driving DB 25*a* and the uncomfortable driving DB 25*b* of the driving data storage unit 25, respectively.

The individual ride model learning unit 26 learns the individual ride model from the comfortable driving data and the uncomfortable driving data (step S103), and stores the model in the individual ride model storage unit 27.

When the driving situation obtaining unit 31 obtains the driving situation of the vehicle in which the subject appears (step S104), the comfortable driving determination unit 32 applies the driving situation to the individual ride model (step S105) to determine the driving that is comfortable for the subject. The comfortable driving information output unit 33 indicates the driving situation necessary for comfortable driving (step S106), and notifies the driver, the passenger, or the automatic vehicle of the driving situation (step S107).

Figure 5:
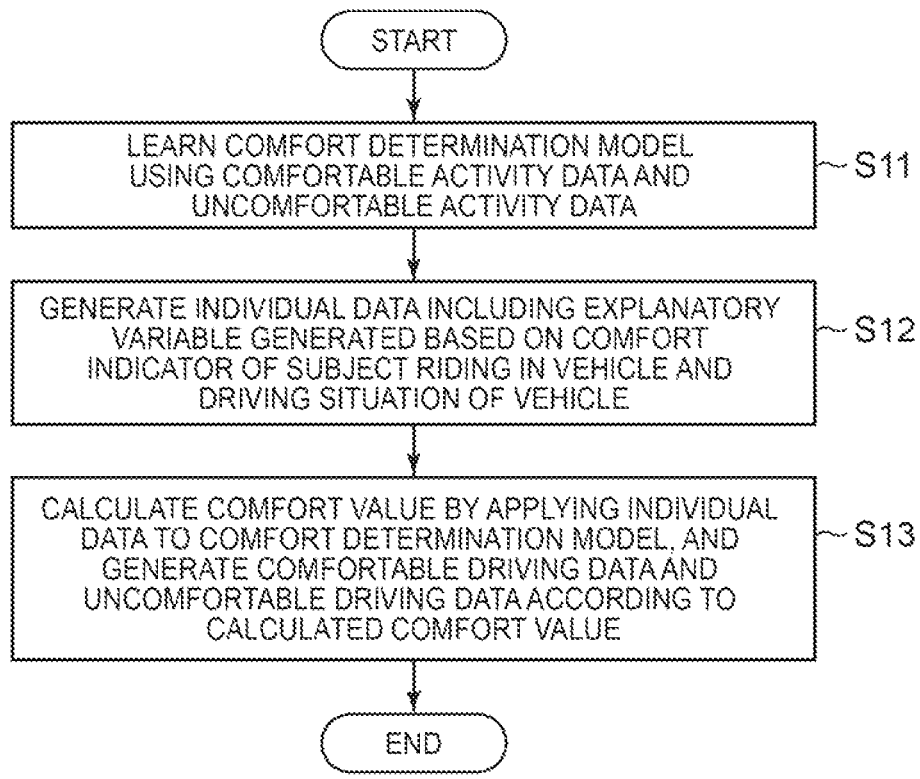
FIG. 5 It depicts a flowchart showing an operation example to collect driving data.

FIG. 5 is a flowchart showing an operation example to collect driving data. The comfort determination model learning unit 14 learns the comfort determination model using the comfortable activity data and the uncomfortable activity data (step S11). The individual data generation unit 22 generates individual data including explanatory variables generated based on comfort indicators of the subject riding in a vehicle, and driving situations of the vehicle (step S12). Then, the driving data generation unit 24 calculates a comfort value by applying the individual data to the comfort determination model, and generates the comfortable driving data and the uncomfortable driving data according to the calculated comfort value (step S13).

Figure 6:
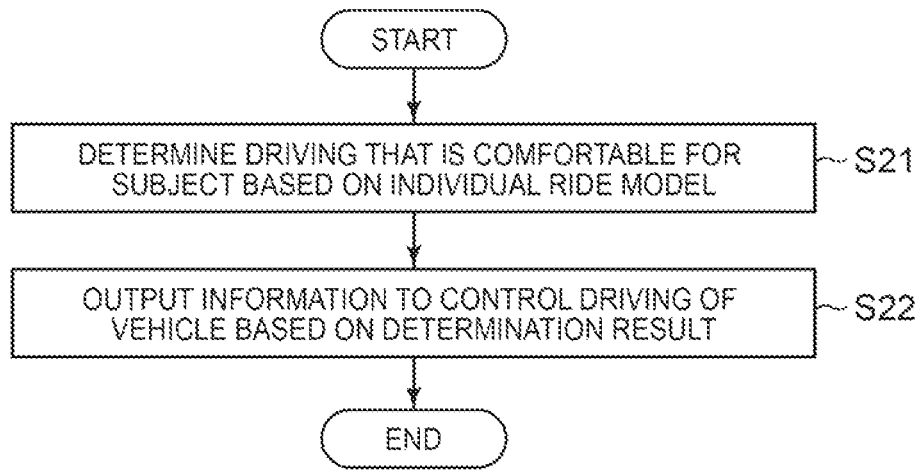
FIG. 6 It depicts a flowchart showing an operation example to control driving of a vehicle.

FIG. 6 is a flowchart showing an operation example to control driving of a vehicle. A comfortable driving determination unit 32 determines, based on the individual ride model, driving that is comfortable for the subject (step S21). The comfortable driving information output unit 33 outputs information to control the driving of the vehicle based on the determination result (step S22).

As described above, in this example embodiment, the comfort determination model learning unit 14 learns the comfort determination model using the comfortable activity data and the uncomfortable activity data, and the individual data generation unit 22 generates individual data including explanatory variables generated based on comfort indicators of the subject riding in a vehicle and situations of the vehicle. Then, the driving data generation unit 24 calculates the comfort value by applying the individual data to the comfort determination model, and generates the comfortable driving data and the uncomfortable driving data according to the calculated comfort value. Thus, data indicating the comfort of a passenger according to a situation during a ride can be efficiently collected.

In addition, in this example embodiment, the comfortable driving determination unit 32 determines the driving that is comfortable for the subject, based on the individual ride model, and the comfortable driving information output unit 33 outputs information to control the driving of the vehicle based on the determination result. Thus, the driving of the vehicle can be controlled to be comfortable for the subject using the data efficiently collected from the subject.

Figure 7:
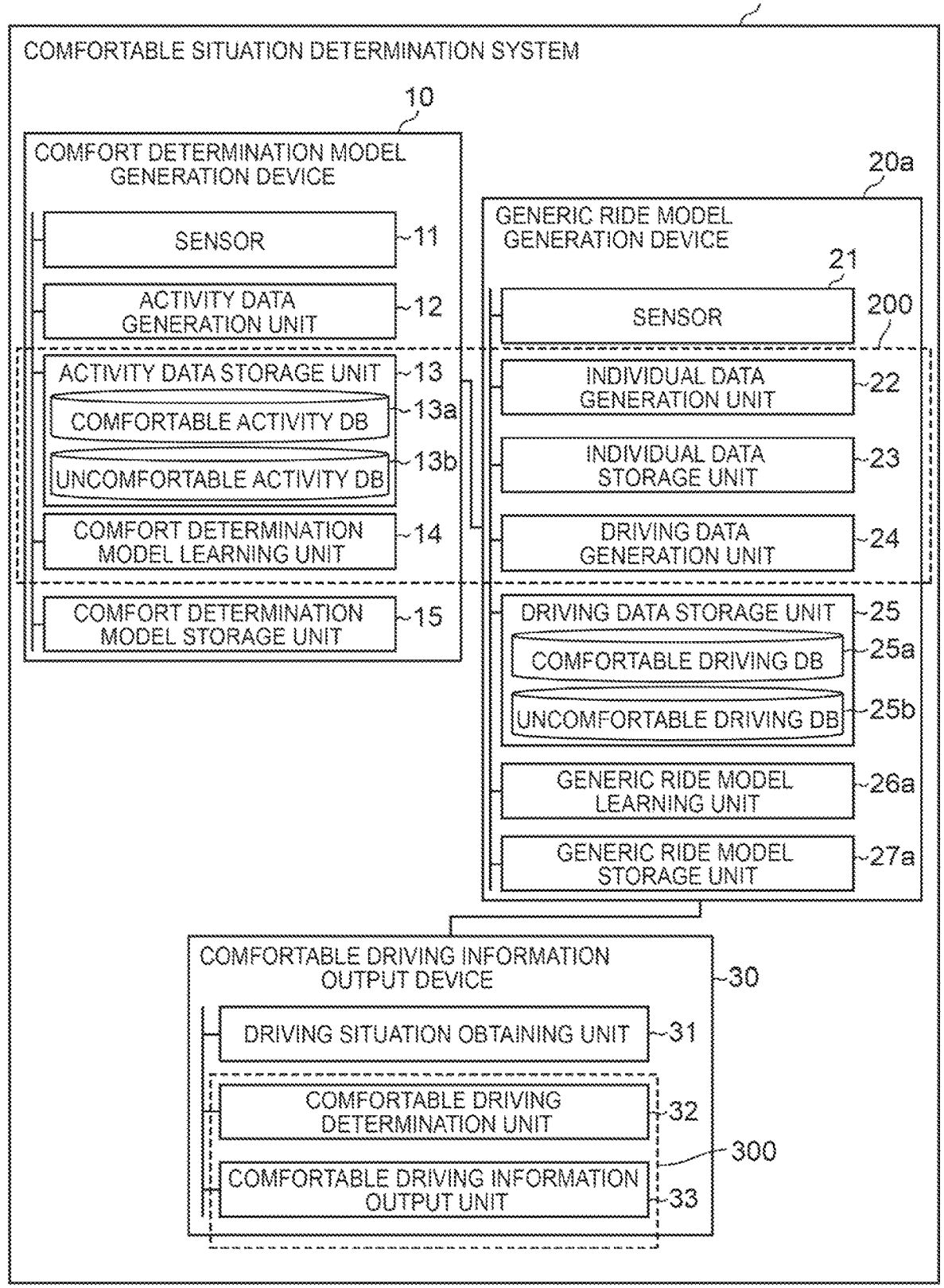
FIG. 7 It depicts a block diagram showing a configuration example of a comfortable situation determination system including a variation of an individual ride model generation device.

Next, a variation of the individual ride model generation device will be described. FIG. 7 is a block diagram showing a configuration example of a comfortable situation determination system 100a including a variation of the individual ride model generation device. The generic ride model generation device 20a of this variation includes a sensor 21, an individual data generation unit 22, an individual data storage unit 23, a driving data generation unit 24, a driving data storage unit 25, a generic ride model learning unit 26a, and a generic ride model storage unit 27a.

In other words, this variation of the comfortable situation determination system 100a differs in that it includes a generic ride model generation device 20a instead of the individual ride model generation device 20 of the above example embodiment, and includes a generic ride model learning unit 26a and a generic ride model storage unit 27a instead of the individual ride model learning unit 26 and the individual ride model storage unit 27 of the above example embodiment. The rest of the configuration is the same as in the above example embodiment. Both the individual ride model generation device 20 and the generic ride model generation device 20a can be said to be devices that learn a ride model of the subject (ride model generation device).

The generic ride model learning unit 26a learns a generic ride model indicating a generic comfort situation according to the driving situation using the generated driving data of a plurality of persons as training data. That is, in the above example embodiment, a ride model is learned for each individual, but in this variation, a generic ride model is generated for a plurality of persons. The method of determining the subjects to be used as training data is arbitrary. For example, the subjects may be determined by gender, age, region, or another unit.

The method by which the generic ride model learning unit 26a learns the generic ride model is arbitrary. The generic ride model learning unit 26a may learn the generic ride model (reward function) using inverse reinforcement learning, as in the above example embodiment. The generic ride model learning unit 26a stores the learned generic ride model in the generic ride model storage unit 27a.

As described above, in this variation, the generic ride model learning unit 26a learns a generic ride model indicating a generic comfort situation according to the driving situation using the generated driving data of a plurality of persons as training data. With such a configuration, a model for determining driving situations for a plurality of persons can be generated. For example, it is possible to improve the accuracy of the ride model even when there is little training data for each individual.

Figure 8:
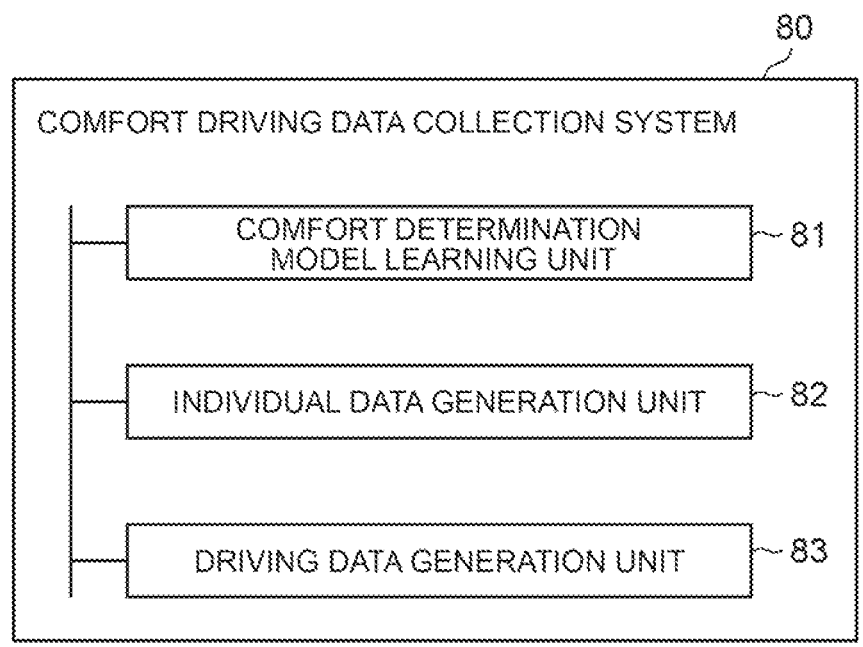
FIG. 8 It depicts a block diagram showing an overview of a comfort driving data collection system according to the exemplary aspect of the present invention.

Next, an overview of the exemplary aspect of the present invention will be described. FIG. 8 is a block diagram showing an overview of a comfort driving data collection system according to the exemplary aspect of the present invention. The comfort driving data collection system 80 (for example, the comfort driving data collection system 200) according to the exemplary aspect of the present invention comprises a comfort determination model learning unit 81 (for example, the comfort determination model learning unit 14) which learns a comfort determination model, by using comfortable activity data where a comfort indicator (for example, heart rate, blink count, etc.), which is an indicator measuring whether an individual is comfortable or not when an activity (for example, watching a favorite TV program, etc.) classified as a comfortable activity is performed, is associated with a teacher label indicating comfort, and uncomfortable activity data where the comfort indicator when an activity (for example, watching an uninteresting TV program, etc.) classified as an uncomfortable activity is performed, is associated with a teacher label indicating discomfort, as first training data, taking an objective variable for a comfort value indicating a degree of comfort, and taking an explanatory variable for each of the comfort indicators, an individual data generation unit 82 (for example, the individual data generation unit 22) which generates, for each subject, individual data including explanatory variables (for example, heart rate, blink count, etc.), which are used in the comfort determination model, generated based on the comfort indicators of the subject during riding on a vehicle, and driving situations (for example, accelerator opening, brake pressure, steering wheel operation angle, etc.) of the vehicle when the comfort indicators are obtained, and a driving data generation unit 83 (for example, the driving data generation unit 24) which calculates the comfort value by applying the individual data to the comfort determination model, and generates driving data indicating a comfortable driving situation and driving data indicating an uncomfortable driving situation according to the calculated comfort value.

With such a configuration, it is possible to efficiently collect data indicating the comfort of a passenger according to the driving situation during a ride.

The comfort driving data collection system 80 may also comprise a ride model learning unit (for example, the individual ride model learning unit 26, the generic ride model learning unit 26a) which learns a ride model indicating a comfortable situation of the subject according to the driving situation, using the driving data indicating a comfortable driving situation and the driving data indicating an uncomfortable driving situation as second training data.

With such a configuration, it is possible to estimate the comfort situation of a passenger using the driving data that can be efficiently collected.

Specifically, the ride model learning unit may learn a ride model by inverse reinforcement learning.

The comfort driving data collection system 80 may also comprise a comfortable driving information output unit (for example, the comfortable driving information output device 30) which outputs a result of comparing the driving situation of the vehicle on which the subject is riding with a determination result by the ride model. With such a configuration, it is possible for the subject to grasp a comfort situation of the passenger using the driving data that can be efficiently collected.

The driving data generation unit may also generate the driving data, as the comfortable driving data, where the driving situation included in the individual data is associated with a comfortable driving flag when the comfort value exceeds the threshold (for example, threshold of 0.5 or the like), and generates the driving data, as the uncomfortable driving data, where the driving situation included in the individual data is associated with an uncomfortable driving flag when the comfort value is below the threshold.

Figure 9:
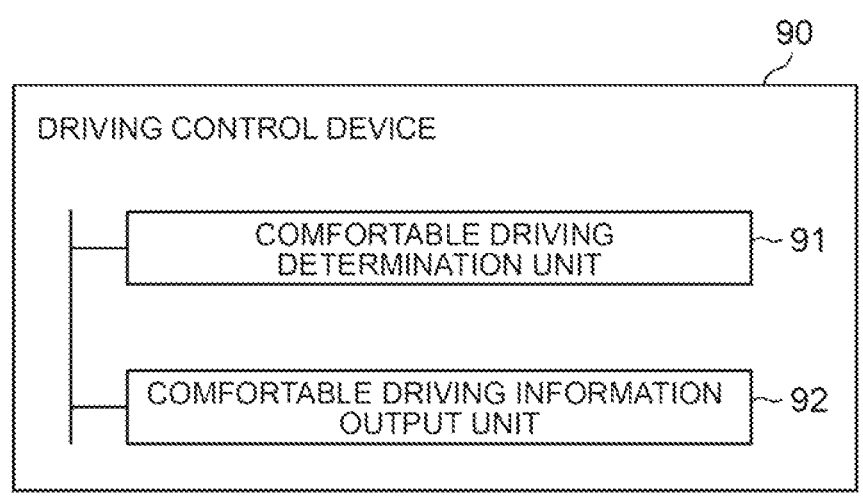
FIG. 9 It depicts a block diagram showing an overview of a driving control device according to the exemplary aspect of the present invention.

FIG. 9 is a block diagram showing an overview of a driving control device according to the exemplary aspect of the present invention. The driving control device 90 (for example, the operation control device 300) according to the present invention comprises a comfortable driving determination unit 91 (for example, the comfortable driving determination unit 32) which determines that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and a comfortable driving information output unit 92 (for example, the comfortable driving information output unit 33) which outputs information to control driving of the vehicle based on a determination result by the comfortable driving determination unit 91.

With such a configuration, it becomes possible that the driving of the vehicle is grasped and controlled to be comfortable for the subject using efficiently collected data indicating the comfort of the passenger according to the situation during a ride.

A part of or all of the above example embodiment may also be described as, but not limited to, the following supplementary notes.

(Supplementary note 1) A comfort driving data collection system comprising:

a comfort determination model learning unit which learns a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, an individual data generation unit which generates, for each subject, individual data including explanatory variables, which are used in the comfort determination model, generated based on the comfort indicators of the subject during riding on a vehicle, and driving situations of the vehicle when the comfort indicators are obtained, and a driving data generation unit which calculates the comfort value by applying the individual data to the comfort determination model, and generates driving data indicating a comfortable driving situation and driving data indicating an uncomfortable driving situation according to the calculated comfort value.

(Supplementary note 2) The comfort driving data collection system according to Supplementary note 1, further comprising a ride model learning unit which learns a ride model indicating a comfortable situation of the subject according to the driving situation, using the driving data indicating a comfortable driving situation and the driving data indicating an uncomfortable driving situation as second training data.

(Supplementary note 3) The comfort driving data collection system according to Supplementary note 2, wherein the ride model learning unit learns the ride model by inverse reinforcement learning.

(Supplementary note 4) The comfort driving data collection system according to Supplementary note 2 or 3, further comprising the comfortable driving information output unit which outputs a result of comparing the driving situation of the vehicle on which the subject is riding with a determination result by the ride model.

(Supplementary note 5) The comfort driving data collection system according to any one of Supplementary notes 1 to 4, wherein the driving data generation unit generates the driving data, as the comfortable driving data, where the driving situation included in the individual data is associated with a comfortable driving flag when the comfort value exceeds the threshold, and generates the driving data, as the uncomfortable driving data, where the driving situation included in the individual data is associated with an uncomfortable driving flag when the comfort value is below the threshold.

(Supplementary note 6) A driving control device comprising:

a comfortable driving determination unit which determines that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and a comfortable driving information output unit which outputs information to control driving of the vehicle based on a determination result by the comfortable driving determination unit.

(Supplementary note 7) A comfort driving data collection method comprising:

learning a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, generating, for each subject, individual data including explanatory variables, which are used in the comfort determination model, generated based on the comfort indicators of the subject during riding on a vehicle, and driving situations of the vehicle when the comfort indicators are obtained, and calculating the comfort value by applying the individual data to the comfort determination model, and generating driving data indicating a comfortable driving situation and driving data indicating an uncomfortable driving situation according to the calculated comfort value.

(Supplementary note 8) The comfort driving data collection method according to Supplementary note 7, further comprising learning a ride model indicating a comfortable situation of the subject according to the driving situation, using the driving data indicating a comfortable driving situation and the driving data indicating an uncomfortable driving situation as second training data.

(Supplementary note 9) A driving control method comprising:

determining that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and outputting information to control driving of the vehicle based on a determination result.

(Supplementary note 10) A comfort driving data collection program causing a computer to execute:

a comfort determination model learning process of learning a comfort determination model, by using comfortable activity data where a comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, taking an objective variable for a comfort value indicating a degree of comfort, and taking an explanatory variable for each of the comfort indicators, an individual data generation process of generating, for each subject, individual data including explanatory variables, which are used in the comfort determination model, generated based on the comfort indicators of the subject during riding on a vehicle, and driving situations of the vehicle when the comfort indicators are obtained, and a driving data generation process of calculating the comfort value by applying the individual data to the comfort determination model, and generating driving data indicating a comfortable driving situation and driving data indicating an uncomfortable driving situation according to the calculated comfort value.

(Supplementary note 11) The comfort driving data collection program according to Supplementary note 10, causing the computer to further execute a ride model learning process of learning a ride model indicating a comfortable situation of the subject according to the driving situation, using the driving data indicating a comfortable driving situation and the driving data indicating an uncomfortable driving situation as second training data.

(Supplementary note 12) A driving control program causing a computer to execute:

a comfortable driving determination process of determining that driving is comfortable for a subject based on a ride model, indicating a comfortable situation of the subject according to a driving situation, learned by using driving data indicating a comfortable driving situation and driving data indicating an uncomfortable driving situation as second training data, generated according to a comfort value obtained by applying individual data including explanatory variables, used in a comfort determination model generated for each subject, based on comfort indicators of the subject riding on a vehicle and the driving situations of the vehicle when the comfort indicators are obtained, to the comfort determination model which is learned by using comfortable activity data where the comfort indicator, which is an indicator measuring whether an individual is comfortable or not when an activity classified as a comfortable activity is performed, is associated with a teacher label indicating comfort, and uncomfortable activity data where the comfort indicator when an activity classified as an uncomfortable activity is performed, is associated with a teacher label indicating discomfort, as first training data, takes an objective variable for a comfort value indicating a degree of comfort, and takes an explanatory variable for each of the comfort indicators, and a comfortable driving information output process of outputting information to control driving of the vehicle based on a determination result.

Although the invention of the present application has been described above with reference to example embodiment and the example, the present invention is not limited to the above example embodiment and the example. Various changes can be made to the configuration and details of the present invention that can be understood by those skilled in the art within the scope of the present invention.

This application claims priority based on Japanese Patent Application No. 2019-133484 filed on Jul. 19, 2019, the disclosure of which is incorporated herein in its entirety.

REFERENCE SIGNS LIST

10 Comfort determination model generation device
11 Sensor

12 Activity data generation unit
13 Activity data storage unit
14 Comfort determination model learning unit
15 Comfort determination model storage unit
20 Individual ride model generation device
20a Generic ride model generation device
21 Sensor
22 Individual data generation unit
23 Individual data storage unit
24 Driving data generation unit
25 Driving data storage unit
26 Individual ride model learning unit
26a Generic ride model learning unit
27 Individual ride model storage unit
27a Generic ride model storage unit
30 Comfortable driving information output device
31 Driving situation obtaining unit
32 Comfortable driving determination unit
33 Comfortable driving information output unit
100 Comfortable situation determination system
200 Comfort driving data collection system
300 Driving control device

The invention claimed is:

1. A comfort driving data collection system comprising:
a memory storing instructions; and
one or more processors configured to execute the instructions to:
 learn a comfort determination model, by using comfortable activity data and uncomfortable activity data as first training data, taking an objective variable for a comfort value indicating a degree of comfort, and taking an explanatory variable for each a comfort indicator, where
  the comfort indicator measures biological information of an individual when activities are performed,
  the comfortable activity data associates the biological information measured by the comfort indicator with a teacher label indicating comfort when an activity classified as a comfortable activity is performed, and
  the uncomfortable activity data associates the biological information measured by the comfort indicator with a teacher label indicating discomfort when an activity classified as an uncomfortable activity is performed;
 generate, for a subject who is riding in a vehicle, individual data including an explanatory variable and driving situations, the explanatory variable used in the comfort determination model and generated based on the comfort indicator measuring the biological information of the subject during riding in the vehicle obtained in the driving situations;
 calculate the comfort value for the subject by applying the comfort determination model to the individual data;
 generate driving data indicating a comfortable driving situation and driving data indicating an uncomfortable driving situation according to the calculated comfort value;
 determine comfort the subject riding in the vehicle based on a ride model learned by using the generated driving data as second training data; and
 control automatic driving of the vehicle based on a result of the determination to increase the comfort of the subject riding in in the vehicle.

2. The system according to claim 1, wherein the processor further executes the instructions to
learn the ride model using the second training data.

3. The comfort driving data collection system according to claim 2, wherein the processor further executes the instructions to
learn the ride model by inverse reinforcement learning.

4. The comfort driving data collection system according to claim 2, wherein the processor further executes instructions to
output a result of comparing a driving situation of the vehicle in which the subject is riding with the result of determination by the ride model.

5. The comfort driving data collection system according to claim 1, wherein the processor further executes the instructions to
generate the driving data as comfortable driving data in which a driving situation included in the individual data is associated with a comfortable driving flag when the calculated comfort value exceeds a threshold, and generate the driving data as uncomfortable driving data in which the driving situation included in the individual data is associated with an uncomfortable driving flag when the comfort value is below the threshold.

6. The system according to claim 1, wherein the driving situations include acceleration of the vehicle when the comfort indicator is obtained.

7. A driving control device comprising:
a memory storing instructions; and
one or more processors configured to execute the instructions to:
determine comfort of a subject riding in a vehicle based on a ride model; and
control automatic driving of the vehicle based on a result of the determination to increase the comfort of the subject riding in in the vehicle,
wherein the ride model is learning by using driving data as second training data,
wherein the driving data indicates a comfortable driving situation and an uncomfortable driving situation according to a comfort value for the subject,
wherein the comfort value for the subject is calculated by applying a comfort determination model to the individual data,
wherein the individual data includes an explanatory variable and driving situations is generated, wherein the explanatory variable is used in the comfort determination model and is generated based on a comfort indicator measuring a biological information of the subject during riding in the vehicle obtained in the driving situation, and
wherein the comfort determination model is learned by using comfortable activity data and uncomfortable activity data as first training data, taking an objective variable for the comfort value indicating a degree of comfort, and taking an explanatory variable for a comfort indicator, where
 the comfort indicator measures the biological information when activities are performed,
 the comfortable activity data associates the biological information measured by the comfort indicator with a teacher label indicating comfort when an activity classified as a comfortable activity is performed, and
 the uncomfortable activity data associates the biological information measured by the comfort indicator with a teacher label indicating discomfort when an activity classified as an uncomfortable activity is performed.

8. A comfort driving data collection method performed by a computer and comprising:
   learning a comfort determination model, by using comfortable activity data and uncomfortable activity data as first training data, taking an objective variable for a comfort value indicating a degree of comfort, and taking an explanatory variable for a comfort indicator, where
   the comfort indicator measures biological information of an individual when activities are performed,
   the comfortable activity data associates the biological information measured by the comfort indicator with a teacher label indicating comfort when an activity classified as a comfortable activity is performed, and
   the uncomfortable activity data associates the biological information measured by the comfort indicator with a teacher label indicating discomfort when an activity classified as an uncomfortable activity is performed;
   generating, for a subject who is riding in a vehicle, individual data including an explanatory variable and driving situations, the explanatory variable used in the comfort determination model and generated based on the comfort indicator measuring the biological information of the subject during riding in the vehicle obtained in the driving situations;
   calculating the comfort value for the subject by applying comfort determination model to the individual data;
   generating driving data indicating a comfortable driving situation and driving data indicating an uncomfortable driving situation according to the calculated comfort value;
   determining comfort the subject riding in the vehicle based on a ride model learned by using the generated driving data as second training data; and
   controlling automatic driving of the vehicle based on a result of the determination to increase the comfort of the subject riding in in the vehicle.

9. The comfort driving data collection method according to claim 8, further comprising
   learning the ride model using the second training data.

* * * * *